United States Patent

Donaldson

[11] Patent Number: 5,971,964
[45] Date of Patent: Oct. 26, 1999

[54] RETRACTABLE SYRINGE

[76] Inventor: Neil Donaldson, 34 Atheling Grove, South Queenferry, West Lothian Scotland EH30 9PF, United Kingdom

[21] Appl. No.: 09/231,372

[22] Filed: Jan. 14, 1999

[51] Int. Cl.⁶ ..................................... A61M 5/00
[52] U.S. Cl. ............................. 604/195; 604/110
[58] Field of Search ..................... 604/195, 192, 604/187, 110, 218, 220

[56] References Cited

U.S. PATENT DOCUMENTS

| | | | |
|---|---|---|---|
| 4,838,869 | 6/1989 | Allard | 604/195 |
| 4,874,382 | 10/1989 | Lindemann et al. | 604/195 |
| 5,295,973 | 3/1994 | Chen | 604/195 |
| 5,342,310 | 8/1994 | Ueyama et al. | 604/110 |
| 5,496,278 | 3/1996 | Buff | 604/110 |

*Primary Examiner*—John D. Yasko

[57] ABSTRACT

A syringe system is providing including a body and a needle assembly including an elongated hollow shaft slidably positioned within the body. Also included is a plunger assembly for expelling fluid from within the body out through the shaft of the needle assembly and further for engaging the needle assembly upon abutment therewith. This allows withdrawal of the shaft of the needle assembly into the body. Next provided is a locking mechanism for precluding reinsertion of the shaft of the needle assembly exterior of the body.

6 Claims, 3 Drawing Sheets

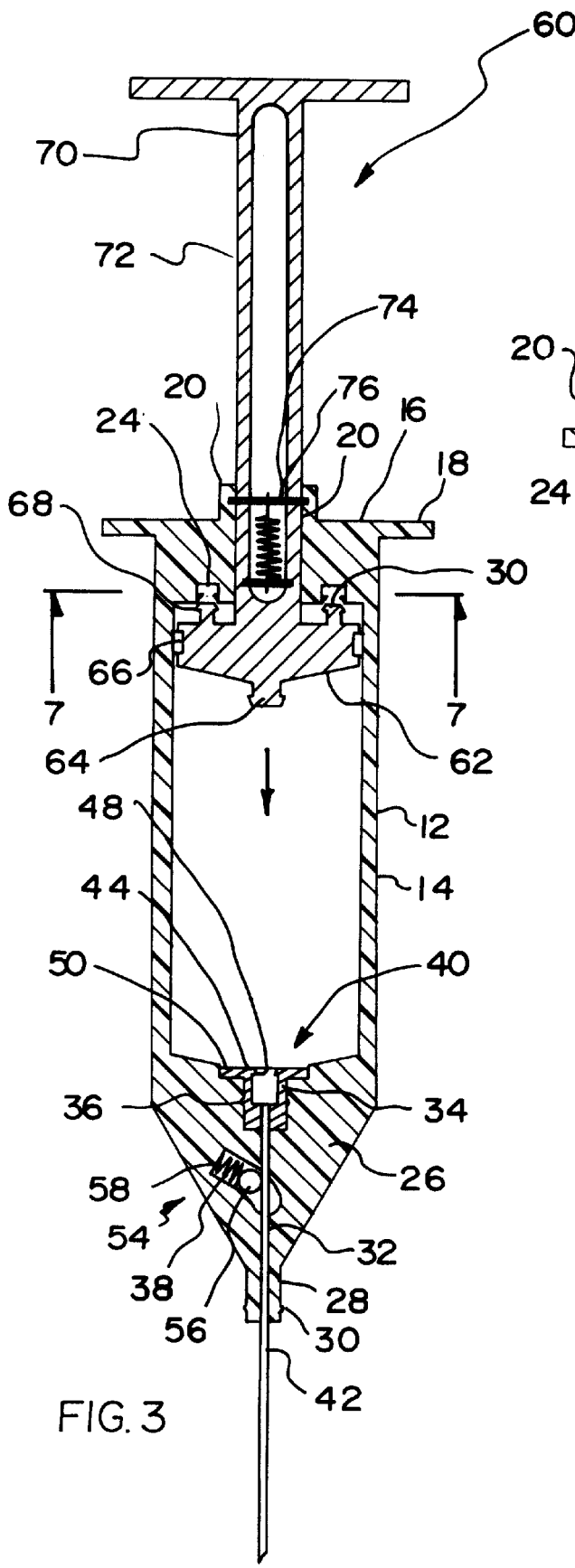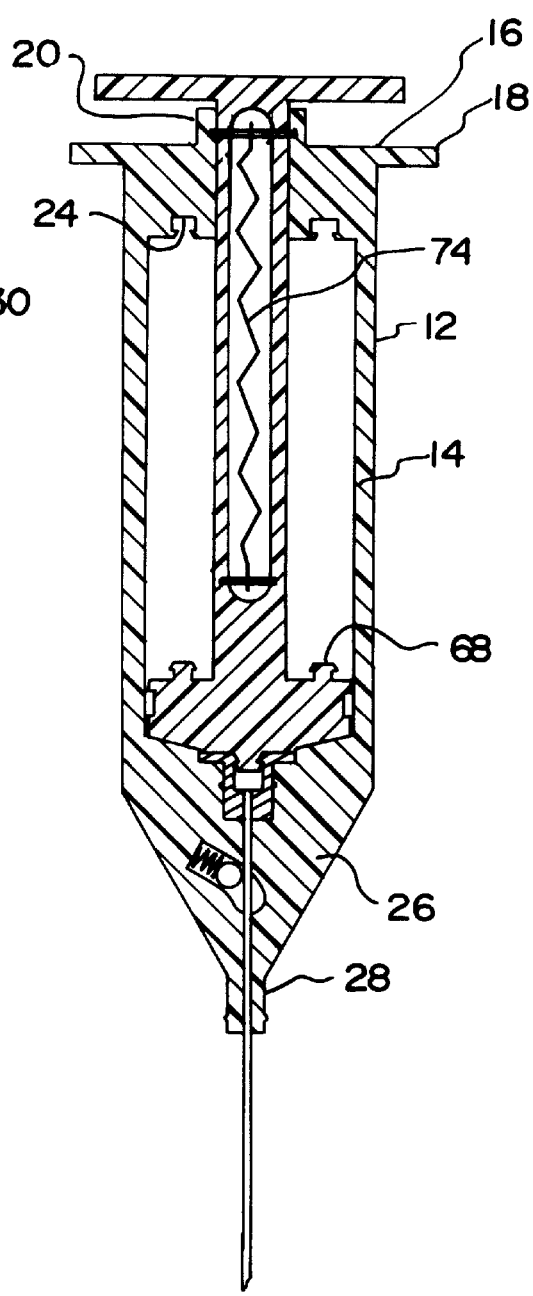

FIG. 5
FIG. 6
FIG. 7
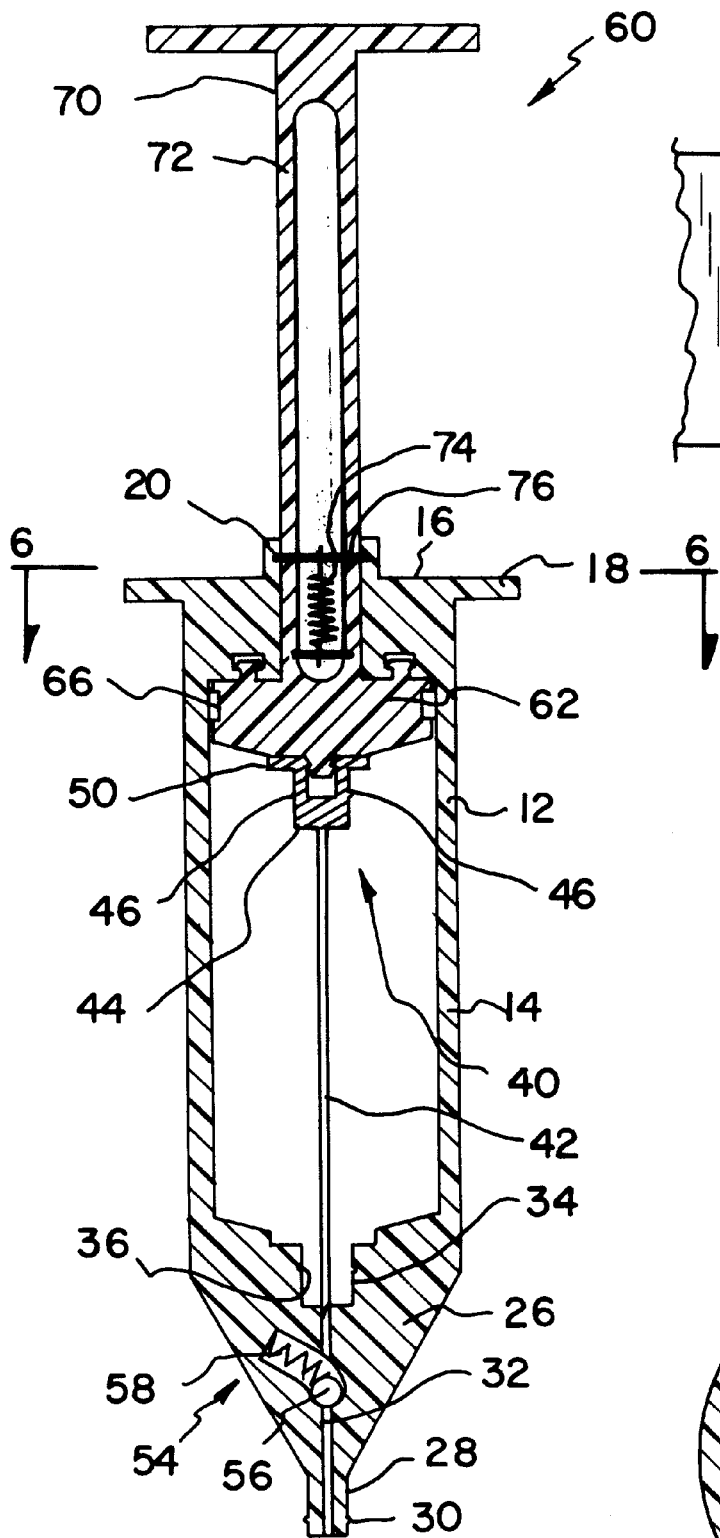
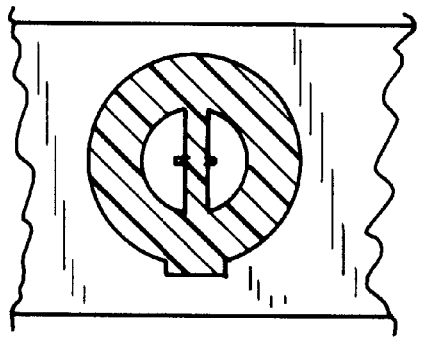
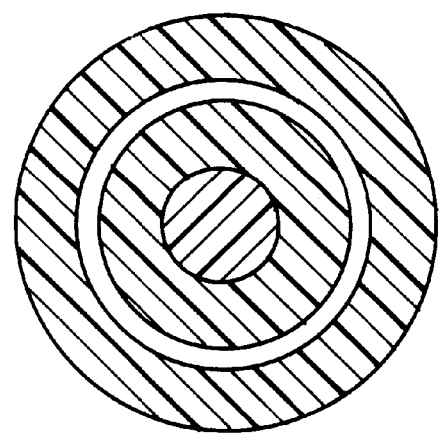

RETRACTABLE SYRINGE

BACKGROUND OF THE INVENTION

1. Field of the Invention

The present invention relates to syringes and more particularly pertains to a new retractable syringe for preventing contact with a needle of a syringe before and after use.

2. Description of the Prior Art

The use of syringes is known in the prior art. More specifically, syringes heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,324,265; U.S. Pat. No. 4,874,382; U.S. Pat. No. 4,995,870; U.S. Pat. No. 5,211,628; U.S. Pat. No. Design 377,687; and U.S. Pat. No. 3,306,291.

In these respects, the retractable syringe according to the present invention substantially departs from the conventional concepts and designs of the prior art, and in so doing provides an apparatus primarily developed for the purpose of preventing contact with a needle of a syringe before and after use.

SUMMARY OF THE INVENTION

In view of the foregoing disadvantages inherent in the known types of syringes now present in the prior art, the present invention provides a new retractable syringe construction wherein the same can be utilized for preventing contact with a needle of a syringe before and after use.

The general purpose of the present invention, which will be described subsequently in greater detail, is to provide a new retractable syringe apparatus and method which has many of the advantages of the syringes mentioned heretofore and many novel features that result in a new retractable syringe which is not anticipated, rendered obvious, suggested, or even implied by any of the prior art syringes, either alone or in any combination thereof.

To attain this, the present invention generally comprises a body having a hollow cylindrical upper portion with a closed top face. As shown in FIG. 1, such top face includes a pair of planar semicircular ears coupled thereto and extending therefrom in coplanar relationship therewith. The top face of the body further has a bore formed therein in coaxial relationship with the body. A sleeve is mounted on an outer surface of the top face and extends outwardly therefrom about the bore. Further, a pair of diametrically opposed female catches are formed in an inner surface of the top face, as shown in FIGS. 3 & 4. The body further includes a conical lower portion having a tubular conduit coupled to an end thereof. Such tubular conduit extends from the lower portion of the body in coaxial relationship and is equipped with an annular detent for reasons that will soon become apparent. As shown in the various Figures, a bore is formed through the lower portion. Further, a cylindrical recess is formed in an inner face of the lower portion with an annular indent formed therein. FIGS. 3–5 show a channel radially extending from the bore of the lower portion to a point adjacent to and spaced from an outer periphery of the lower portion of the body. Also included is a needle assembly having an elongated hollow shaft positioned within the bore of the lower portion of the body. Such shaft of the needle assembly is equipped with a sharpened first end positioned exterior of the body. Further, the present invention has a cap including a circular bottom face coupled to a second end of the shaft. As shown in FIGS. 3–5, the cap is equipped with a peripheral side wall coupled to a periphery of the bottom face of the cap and extends upwardly therefrom to define a hollow interior. An annular detent is formed on a central extent of an outer surface of the peripheral side wall of the cap for engaging the annular indent of the cylindrical recess of the lower portion of the body. For reasons that will soon become apparent, a female catch is defined within an inner surface of the peripheral side wall of the cap. Next provided is a cover with an elongated generally cylindrical configuration including a closed bottom end and an open top end. An annular indent is formed in the cover adjacent the open top end and for engaging the annular detent of the tubular conduit of the body. In use, the cover encloses the shaft of the need assembly when the top end of the cover is received by the tubular conduit of the body. With reference again to FIGS. 3–4, a locking mechanism is shown to include a ball bearing slidably positioned within the channel of the lower portion of the body. A coil spring is also positioned within the channel for urging the ball bearing against the shaft of the needle assembly. Finally, a plunger assembly is provided including a piston with a generally disk-shaped configuration slidably positioned within the upper portion of the body. Such piston has a bottom face with a male catch centrally formed thereon. A periphery of the piston is equipped with an O-ring for creating a seal with the upper portion of the body. The piston further has a top face with a pair of diametrically opposed pair of male catches. The plunger assembly further includes a handle rod connected to the top face of the piston and extending upwardly therefrom in sliding relationship with the bore formed in the top face of the upper portion of the body. It should be noted that the handle rod has a longitudinal, diametrically disposed slot formed along a length thereof. The plunger assembly further includes a coil spring with a first end connected within the handle rod adjacent to a bottom end thereof. A second end of the coil spring is connected to a member coupled within the bore of the top face of the upper portion of the body and slidably positioned within the slot of the handle rod. In use, the spring urges handle rod in an extended orientation. In operation, upon the depression of the handle rod to a retracted orientation, fluid within the body is expelled from the shaft of the needle assembly and the male catch of the bottom face of the piston engages the female catch of the cap of the needle assembly. Thereafter, the handle rod and the needle assembly are together urged by the spring thereof into the extended orientation. As such, the ball bearing of the locking mechanism may be moved in alignment within the bore of the lower portion of the body to preclude reinsertion of the needle therein. Upon full extension of the handle rod, the male catches of the top face of the piston of the plunger assembly engage the female catches of the top face of the body, thereby maintaining the same in the extended orientation.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new retractable syringe apparatus and method which has many of the advantages of the syringes mentioned heretofore and many novel features that result in a new retractable syringe which is not anticipated, rendered obvious, suggested, or even implied by any of the prior art syringes, either alone or in any combination thereof.

It is another object of the present invention to provide a new retractable syringe which may be easily and efficiently manufactured and marketed.

It is a further object of the present invention to provide a new retractable syringe which is of a durable and reliable construction.

An even further object of the present invention is to provide a new retractable syringe which is susceptible of a low cost of manufacture with regard to both materials and labor, and which accordingly is then susceptible of low prices of sale to the consuming public, thereby making such retractable syringe economically available to the buying public.

Still yet another object of the present invention is to provide a new retractable syringe which provides in the apparatuses and methods of the prior art some of the advantages thereof, while simultaneously overcoming some of the disadvantages normally associated therewith.

Still another object of the present invention is to provide a new retractable syringe for preventing contact with a needle of a syringe before and after use.

Even still another object of the present invention is to provide a new retractable syringe that includes a body and a needle assembly including an elongated hollow shaft slidably positioned within the body. Also included is a plunger assembly for expelling fluid from within the body out through the shaft of the needle assembly and further for engaging the needle assembly upon abutment therewith. This allows withdrawal of the shaft of the needle assembly into the body. Next provided is a locking mechanism for precluding reinsertion of the shaft of the needle assembly exterior of the body.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross-sectional view of the present invention taken prior to use of the present invention.

FIG. 4 is a cross-sectional view of the present invention taken upon the plunger assembly being inserted within a user to expel fluids from the shaft of the needle assembly.

FIG. 5 is a cross-sectional view of the present invention taken upon the automatic extension of the plunger assembly and the enablement of the locking mechanism.

FIG. 6 is a cross-sectional view of the handle rod of the present invention taken along line 6—6 shown in FIG. 5.

FIG. 7 is a cross-sectional view of the present invention taken along line 7—7 shown in FIG. 3.

DESCRIPTION OF THE PREFERRED EMBODIMENT

Figure 1:
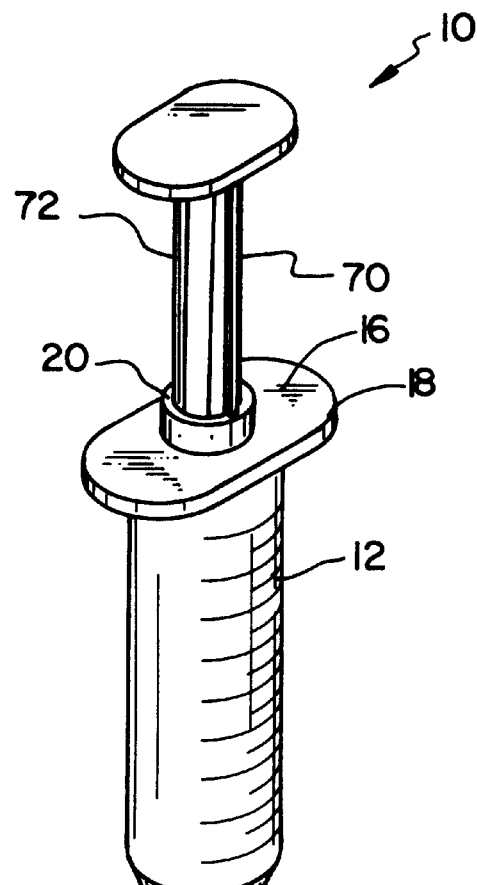
FIG. 1 is a perspective view of a new retractable syringe according to the present invention.
Figure 2:
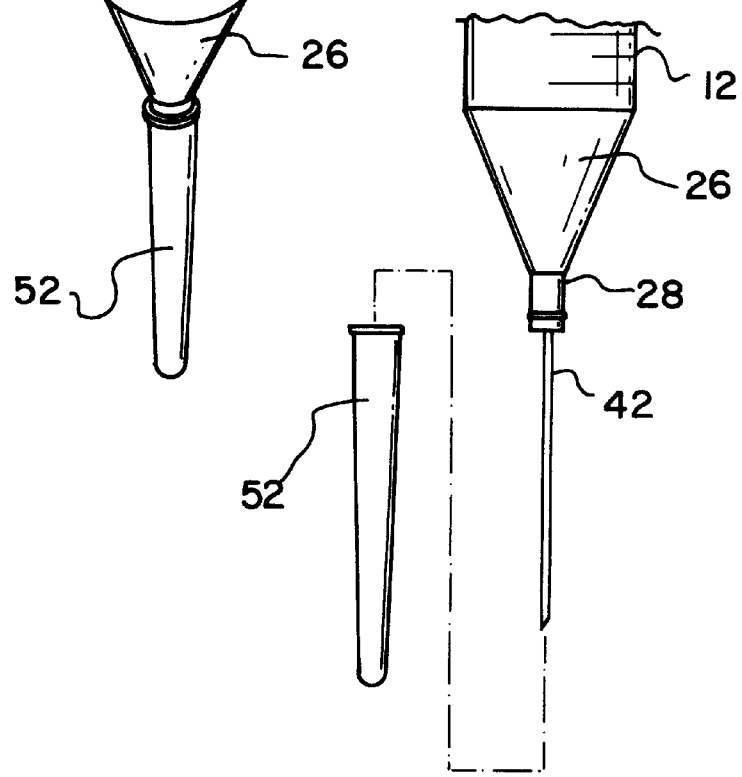
FIG. 2 is an exploded view of the present invention with the cover thereof removed.

With reference now to the drawings, and in particular to FIGS. 1 through 7 thereof, a new retractable syringe embodying the principles and concepts of the present invention and generally designated by the reference numeral 10 will be described.

The present invention, designated as numeral 10, includes a body 12 having a hollow cylindrical upper portion 14 with a closed top face 16. As shown in FIG. 1, such top face includes a pair of planar semicircular ears 18 coupled thereto and extending therefrom in coplanar relationship therewith. The top face of the body further has a large bore 20 formed therein in coaxial relationship with the body. A sleeve 22 is mounted on an outer surface of the top face and extends outwardly therefrom about the bore. Further, a pair of diametrically opposed female catches 24 are formed in an inner surface of the top face, as shown in FIGS. 3 & 4. The body further includes a conical lower portion 26 having a tubular conduit 28 coupled to an end thereof. Such tubular conduit extends from the lower portion of the body in coaxial relationship and is equipped with an annular detent 30 for reasons that will soon become apparent.

As shown in the various Figures, a small bore 32 is formed through the lower portion of the body. Further, a cylindrical recess 34 is formed in an inner face of the lower portion with an annular indent 36 formed therein. FIGS. 3–5 show a channel 38 radially extending from the bore of the lower portion to a point adjacent to and spaced from an outer periphery of the lower portion of the body.

Also included is a needle assembly 40 having an elongated hollow shaft 42 positioned within the bore of the lower portion of the body. Such shaft of the needle assembly is equipped with a sharpened first end positioned exterior of the body. Further, the present invention has a cap 44 including a circular bottom face coupled to a second end of the shaft. As shown in FIGS. 3–5, the cap is equipped with a peripheral side wall coupled to a periphery of the bottom face of the cap and extends upwardly therefrom to define a hollow interior. An annular detent 46 is formed on a central extent of an outer surface of the peripheral side wall of the cap for engaging the annular indent of the cylindrical recess of the lower portion of the body. For reasons that will soon become apparent, a female catch 48 is defined within an inner surface of the peripheral side wall of the cap. As an option, the cap may further be equipped with a radially extending annular flange 50.

Next provided is a cover 52 with an elongated slightly tapering, generally cylindrical configuration including a closed bottom end and an open top end. An annular indent is formed in the cover adjacent the open top end for engaging the annular detent of the tubular conduit of the body. In use, the cover encloses the shaft of the need assembly when the top end of the cover is received by the tubular conduit of the body.

With reference again to FIGS. 3–4, a locking mechanism 54 is shown to include a ball bearing 56 slidably positioned within the channel of the lower portion of the body. A coil spring 58 is also positioned within the channel for urging the ball bearing against the shaft of the needle assembly. A shown in the Figures, the channel preferably extends radially and toward the top face of body.

Finally, a plunger assembly 60 is provided including a piston 62 with a generally disk-shaped configuration slidably positioned within the upper portion of the body. Such piston has a bottom face with a male catch 64 centrally formed thereon. A periphery of the piston is equipped with an O-ring 66 for creating a seal with the upper portion of the body. The piston further has a top face with a pair of diametrically opposed of male catches 68. Ideally, each of the catches is defined by a protrusion or recess with an outwardly or inwardly extending lip, respectively, which has a triangular cross-section. It should be noted that the catches 24 & 68 may also constitute single annular or ring-like catches per the desires of the user.

The plunger assembly further includes a handle rod 70 connected to the top face of the piston and extending upwardly therefrom in sliding relationship with the bore formed in the top face of the upper portion of the body. It should be noted that the handle rod has a longitudinal, diametrically disposed slot 72 formed along a length thereof. The plunger assembly further includes a coil spring 74 with a first end connected within the handle rod adjacent to a bottom end thereof. A second end of the coil spring is connected to a member 76 coupled within the bore of the top face of the upper portion of the body via a collar and slidably positioned within the slot of the handle rod. In use, the spring urges handle rod in an extended orientation.

In operation, upon the depression of the handle rod to a retracted orientation, fluid within the body is expelled from the shaft of the needle assembly and the male catch of the bottom face of the piston engages the female catch of the cap of the needle assembly. Note FIG. 4. Thereafter, the handle rod and the needle assembly are together urged by the spring thereof into the extended orientation. As such, the ball bearing of the locking mechanism may be moved in alignment within the bore of the lower portion of the body to preclude reinsertion of the needle therein. Upon full extension of the handle rod, the male catches of the top face of the piston of the plunger assembly engage the female catches of the top face of the body, thereby maintaining the same in the extended orientation. See FIG. 5. In order to accomplish this, the frictional force between the annular indents and detents of the cap of the needle assembly and body is sufficient to withstand insertion of the shaft of the needle assembly into a user while being less than the frictional forces associated with the female and male catches.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A syringe system comprising, in combination:

a body having a hollow cylindrical upper portion with a closed top face including a pair of planar semicircular ears coupled thereto and extending therefrom in coplanar relationship therewith, the top face further having a bore formed therein in coaxial relationship with the body, a sleeve mounted on an outer surface of the top face and extending outwardly therefrom about the bore, and a pair of diametrically opposed female catches formed in an inner surface of the top face, the body further including a conical lower portion having a tubular conduit coupled to an end thereof and extending therefrom in coaxial relationship with the lower portion with an annular detent, a bore formed through the lower portion, a cylindrical recess formed in an inner face of the lower portion with an annular indent formed therein, and a channel radially extending from the bore of the lower portion to a point adjacent to and spaced from an outer periphery of the lower portion of the body;

a needle assembly including an elongated hollow shaft positioned within the bore of the lower portion of the body with a sharpened first end positioned exterior of the body and a cap including a circular bottom face coupled to a second end of the shaft and a peripheral side wall coupled to a periphery of the bottom face of the cap and extending upwardly therefrom to define a hollow interior with an annular detent formed on a central extent of an outer surface of the peripheral side wall of the cap for engaging the annular indent of the cylindrical recess of the lower portion of the body and a female catch defined within an inner surface of the peripheral side wall of the cap;

a cover with an elongated generally cylindrical configuration including a closed bottom end, an open top end, and an annular indent for engaging the annular detent of the tubular conduit of the body, wherein the cover encloses the shaft of the need assembly when the top end of the cover is received by the tubular conduit of the body;

a locking mechanism including ball bearing slidably positioned within the channel of the lower portion of the body and a coil spring positioned within the channel for urging the ball bearing against the shaft of the needle assembly; and a plunger assembly including a piston with a generally disk-shaped configuration slidably positioned within the upper portion of the body and having a bottom face with a male catch centrally formed thereon, a periphery with an O-ring for creating a seal with the upper portion of the body, and a top face with a pair of diametrically opposed pair of male catches, the plunger assembly further including a handle rod connected to the top face of the piston and extending upwardly therefrom in sliding relationship with the bore formed in the top face of the upper portion of the body, the handle rod having a longitudinal, diametrically disposed slot formed along a length thereof, the plunger assembly further including a coil spring with a first end connected within the handle rod adjacent to a bottom end thereof and a second end connected to a member coupled within the bore of the top face of the upper portion of the body and slidably positioned within the slot of the handle rod, wherein the spring urges handle rod in an extended orientation;

wherein upon the depression of the handle rod to a retracted orientation, fluid within the body is expelled from the shaft of the needle assembly and the male catch of the bottom face of the piston engages the female catch of the cap of the needle assembly whereafter the handle rod and the needle assembly are urged by the spring thereof into the extended orientation and the ball bearing of the locking mechanism is moved in alignment within the bore of the lower portion of the body to preclude reinsertion of the needle therein and further the male catches of the top face of the piston of the plunger assembly engage the female catches of the top face of the body.

2. A syringe system comprising:

a body;

a needle assembly including an elongated hollow shaft slidably positioned within the body;

a plunger assembly for expelling fluid from within the body out through the shaft of the needle assembly and further for engaging the needle assembly upon abutment therewith, thereby allowing withdrawal of the shaft of the needle assembly into the body;

a locking mechanism for precluding reinsertion of the shaft of the needle assembly exterior of the body;

wherein the locking mechanism includes a radially extending channel within the body with a spring loaded stop for sliding in alignment with the shaft of the needle assembly upon the withdrawal of the shaft of the needle assembly into the body.

3. A syringe system as set forth in claim 2 wherein the plunger assembly includes a handle rod with a spring therein which is attached to the body for urging the handle into an extended orientation.

4. A syringe system as set forth in claim 2 wherein the body has at least one catch for engaging the piston assembly upon the same being transferred to the extended orientation.

5. A syringe system as set forth in claim 2 wherein the needle assembly includes a female catch defined by an inwardly extending flange for engaging an outwardly extending flange of a male catch mounted on the piston assembly.

6. A syringe system comprising, in combination:

a body having a hollow upper portion with a closed top face including a pair of ears coupled thereto and extending therefrom;

the top face further having a bore formed therein in, a sleeve mounted on an outer surface of the top face and extending outwardly therefrom about the bore, and a pair of female catches formed in an inner surface of the top face;

the body further including a lower portion having a conduit with an annular detent, a bore formed through the lower portion, a recess formed in an inner face of the lower portion with an annular indent formed therein, and a channel radially extending from the bore of the lower portion to a point adjacent to and spaced from an outer periphery of the lower portion of the body;

a needle assembly including an elongated hollow shaft positioned in the bore of the lower portion of the body with a sharpened first end positioned exterior of the body and a cap including a bottom face coupled to a second end of the shaft and a peripheral side wall coupled to a periphery of the bottom face of the cap and extending upwardly therefrom to define a hollow interior with an annular detent formed on a central extent of an outer surface of the peripheral side wall of the cap for engaging the annular indent of the recess of the lower portion of the body and a female catch defined within an inner surface of the peripheral side wall of the cap;

a locking mechanism including ball bearing slidably positioned within the channel of the lower portion of the body and a coil spring positioned within the channel for urging the ball bearing against the shaft of the needle assembly; and a plunger assembly including a piston slidably positioned within the upper portion of the body, the piston being coupled to the needle assembly.

* * * * *